(12) United States Patent
Liu

(10) Patent No.: US 12,048,338 B2
(45) Date of Patent: Jul. 30, 2024

(54) WEARABLE ORTHOPEDIC DEVICE FOR LOWER BODY POSTURE CORRECTION AND IMPROVED ERGONOMICS

(71) Applicant: IFGCure Holdings, LLC, Los Angeles, CA (US)

(72) Inventor: Stephen H. Liu, Los Angeles, CA (US)

(73) Assignee: IFGCure Holdings, LLC, Los Angeles, CA (US)

(*) Notice: Subject to any disclaimer, the term of this patent is extended or adjusted under 35 U.S.C. 154(b) by 87 days.

(21) Appl. No.: 16/827,614

(22) Filed: Mar. 23, 2020

(65) Prior Publication Data
US 2020/0253291 A1     Aug. 13, 2020

Related U.S. Application Data

(63) Continuation-in-part of application No. 29/714,475, filed on Nov. 22, 2019, now Pat. No. Des. 921,330, and a continuation-in-part of application No. 29/714,472, filed on Nov. 22, 2019, now Pat. No. Des. 921,329, and a continuation-in-part of application No. 16/368,588, filed on Mar. 28, 2019, now Pat. No. 10,736,364, which is a continuation-in-part of application No. 16/147,639, filed on Sep. 29, 2018, now abandoned, which is a continuation of application No. 16/125,453, filed on Sep. 7, 2018, now Pat. No. 10,721,975, which is a continuation-in-part of application No. 16/057,558,
(Continued)

(51) Int. Cl.
A41D 1/08     (2018.01)

(52) U.S. Cl.
CPC ............ *A41D 1/08* (2013.01); *A41B 2300/22* (2013.01); *A41B 2400/32* (2013.01)

(58) Field of Classification Search
CPC .. A41D 1/08; A41B 2300/22; A41B 2400/32; A41C 1/003; A61F 5/026
USPC ........................................................... 2/227
See application file for complete search history.

(56) References Cited

U.S. PATENT DOCUMENTS

| 162,580 A | 4/1875 | Schandevyl |
| 245,524 A | 8/1881 | Lubin |

(Continued)

FOREIGN PATENT DOCUMENTS

| CN | 2922842 | 7/2007 |
| CN | 201048997 | 4/2008 |

(Continued)

OTHER PUBLICATIONS

International Search Report PCT/US2018/041162 Completed Oct. 17, 2018; Mailed Oct. 30, 2018 6 pages.
(Continued)

*Primary Examiner* — Jocelyn Bravo
(74) *Attorney, Agent, or Firm* — Ferguson Case Orr Paterson

(57) ABSTRACT

The present disclosure is directed to a wearable orthopedic device for lower body posture correction and improve human ergonomics. Embodiments of the present disclosure include pairs of men's and women's shorts that have specially positioned and tensioned panels for providing a wearer with a neutral pelvis. In certain embodiments, the device targets the body's proprioceptors to train the body to properly align itself.

20 Claims, 10 Drawing Sheets

Related U.S. Application Data filed on Aug. 7, 2018, now abandoned, which is a continuation-in-part of application No. 16/029,567, filed on Jul. 7, 2018, now abandoned.

(60) Provisional application No. 62/649,542, filed on Mar. 28, 2018.

(56) References Cited

U.S. PATENT DOCUMENTS

| | | | |
|---|---|---|---|
| 559,024 A | 4/1896 | Bessing | |
| 664,250 A | 12/1900 | Fitzpatrick | |
| 1,075,348 A | 10/1913 | Fritsch | |
| 1,129,515 A | 2/1915 | Perry | |
| 1,293,089 A | 2/1919 | Hardy | |
| 1,401,227 A | 12/1921 | Wyeth | |
| 1,650,650 A | 11/1927 | Pieper | |
| 1,766,278 A | 6/1930 | Bollwine | |
| 1,804,855 A | 5/1931 | Bollwine | |
| 2,009,620 A | 7/1935 | Jackson | |
| 2,100,932 A | 11/1937 | Louis | |
| 2,211,549 A | 8/1940 | Semons | |
| 2,255,931 A * | 9/1941 | Kloster | A41B 9/02 2/404 |
| 2,310,855 A | 2/1943 | Manson | |
| 2,327,488 A | 8/1943 | Becker | |
| 2,443,316 A | 6/1948 | Israel | |
| 2,581,036 A | 1/1952 | McIlhinney | |
| 2,585,567 A | 2/1952 | Marin | |
| 2,591,462 A | 4/1952 | Mungo | |
| 2,629,094 A * | 2/1953 | Goldsmith | A41D 13/0575 2/467 |
| 2,654,091 A | 10/1953 | Nelson | |
| 2,752,601 A | 7/1956 | Gluckin | |
| 2,782,416 A | 2/1957 | Ginsburg | |
| 2,800,659 A | 7/1957 | Hazard | |
| 2,881,764 A | 4/1959 | Verreault | |
| 3,008,468 A | 11/1961 | Helene | |
| 3,027,898 A | 4/1962 | Helene | |
| 3,066,676 A | 12/1962 | Kaupp | |
| 3,077,198 A | 2/1963 | Williamson | |
| 3,116,735 A | 1/1964 | Geimer | |
| 3,141,456 A | 7/1964 | Meek | |
| 3,144,869 A | 8/1964 | Blair | |
| 3,182,655 A | 5/1965 | Nelkin | |
| 3,186,412 A | 6/1965 | Kurland | |
| 3,277,889 A | 10/1966 | Palmer | |
| 3,310,053 A * | 3/1967 | Greenwood | A41C 1/00 450/153 |
| 3,338,236 A | 8/1967 | McLeod, Jr. | |
| 3,430,632 A | 3/1969 | Emily | |
| 3,470,570 A | 10/1969 | Christiansen | |
| 3,515,142 A * | 6/1970 | Rockwell | A41C 1/02 450/109 |
| 3,568,681 A | 3/1971 | Comollo | |
| 3,606,891 A | 9/1971 | Marcario | |
| 3,637,230 A * | 1/1972 | Poik | A63C 11/00 280/18 |
| 3,653,075 A | 4/1972 | Gluckin | |
| 3,813,697 A * | 6/1974 | Belpaume | A41D 1/089 2/238 |
| 3,856,004 A | 12/1974 | Cox | |
| 3,894,542 A * | 7/1975 | Sacristan | A41C 1/003 450/123 |
| 3,996,622 A * | 12/1976 | Cooke | A41D 1/06 2/227 |
| 4,202,327 A | 5/1980 | Glancy | |
| 4,261,060 A * | 4/1981 | Zawacki | A41D 1/084 2/238 |
| 4,289,137 A | 9/1981 | Dell | |
| 4,341,219 A | 7/1982 | Kuznetz | |
| 4,398,538 A | 8/1983 | Johnson | |
| 4,479,269 A * | 10/1984 | Balliet | A41D 13/0593 2/23 |
| 4,507,801 A * | 4/1985 | Kavanagh | A41D 13/015 2/267 |
| 4,538,614 A | 9/1985 | Henderson | |
| 4,625,336 A * | 12/1986 | Derderian | A41D 13/0015 2/409 |
| 4,638,513 A | 1/1987 | Woods | |
| 4,698,847 A | 10/1987 | Yoshihara | |
| 4,741,719 A | 5/1988 | Wirth | |
| 4,781,651 A | 11/1988 | Ekins | |
| 4,791,685 A * | 12/1988 | Maibauer | A41D 27/28 2/46 |
| 4,805,243 A * | 2/1989 | Gibbens | A41D 1/084 2/253 |
| 4,816,005 A | 3/1989 | Braaten | |
| 4,850,056 A * | 7/1989 | Gardner | A41D 1/08 2/227 |
| 4,957,103 A | 9/1990 | Young | |
| 4,971,073 A | 11/1990 | Schneider | |
| 5,018,513 A | 5/1991 | Charles | |
| 5,045,019 A | 9/1991 | Capasso | |
| 5,052,058 A * | 10/1991 | Mueller | D04B 21/207 66/177 |
| 5,109,546 A * | 5/1992 | Dicker | A41D 13/0015 482/121 |
| 5,120,264 A | 6/1992 | Van Engel | |
| 5,158,531 A | 10/1992 | Zamosky | |
| 5,210,877 A * | 5/1993 | Newman | A41D 1/067 2/243.1 |
| 5,259,833 A | 11/1993 | Barnett | |
| 5,451,200 A | 9/1995 | Labella | |
| 5,466,214 A | 11/1995 | Calderon-Garciduenas | |
| 5,537,690 A | 7/1996 | Johnson | |
| 5,599,286 A | 2/1997 | Labelle | |
| 5,662,512 A | 9/1997 | Cohen | |
| 5,689,836 A * | 11/1997 | Fee | A41D 13/0593 2/22 |
| 5,718,670 A | 2/1998 | Bremer | |
| 5,765,224 A | 6/1998 | Johnson | |
| 5,823,851 A | 10/1998 | Dicker | |
| 5,839,942 A | 11/1998 | Miller | |
| 5,873,767 A | 2/1999 | Pickett | |
| 5,897,422 A | 4/1999 | McGee | |
| 5,902,261 A | 5/1999 | Schwartz | |
| 5,968,003 A | 10/1999 | Sisson | |
| 6,023,789 A * | 2/2000 | Wilson | A41D 1/089 2/404 |
| 6,041,441 A * | 3/2000 | Counts | A41D 13/0575 450/150 |
| 6,068,538 A | 5/2000 | Alleyne | |
| 6,102,879 A | 8/2000 | Christensen | |
| 6,168,498 B1 | 1/2001 | Wagner | |
| 6,190,342 B1 | 2/2001 | Taylor | |
| 6,192,521 B1 * | 2/2001 | Alberts | A61F 13/496 2/400 |
| 6,213,922 B1 | 4/2001 | Afanasenko | |
| 6,243,878 B1 * | 6/2001 | Khemka | A41D 1/065 2/234 |
| 6,243,880 B1 * | 6/2001 | Lyden | A41B 9/02 2/400 |
| 6,280,287 B1 | 8/2001 | Keith | |
| 6,315,747 B1 | 11/2001 | Toole | |
| 6,319,092 B1 | 11/2001 | Leyhe | |
| 6,346,027 B1 | 2/2002 | Merkovsky | |
| 6,363,538 B1 * | 4/2002 | Davis | A41D 1/089 2/238 |
| 6,387,067 B1 | 5/2002 | Hebert | |
| 6,401,250 B1 * | 6/2002 | McNabb | A41D 1/06 2/78.2 |
| 6,440,094 B1 | 8/2002 | Maas | |
| 6,443,805 B1 | 9/2002 | Kirkwood | |
| 6,530,820 B1 | 3/2003 | Katze | |
| 6,575,811 B1 | 6/2003 | Fildan | |
| 6,676,617 B1 | 1/2004 | Miller | |
| 6,795,213 B1 | 9/2004 | Hanyu | |
| 6,795,215 B1 | 9/2004 | Silverbrook | |
| 6,846,217 B1 | 1/2005 | Struble | |
| 6,846,219 B2 | 1/2005 | Moyer | |
| 6,860,789 B2 | 3/2005 | Bell | |

(56) References Cited

U.S. PATENT DOCUMENTS

| | | | |
|---|---|---|---|
| D505,753 S * | 5/2005 | Qvortrup | D29/100 |
| 6,936,021 B1 | 8/2005 | Smith | |
| 7,017,193 B2 * | 3/2006 | Auger | A41B 9/023 |
| | | | 2/403 |
| 7,134,969 B2 | 11/2006 | Citron | |
| 7,153,246 B2 | 12/2006 | Koscielny | |
| 7,395,557 B1 | 7/2008 | Ledyard | |
| 7,533,423 B2 * | 5/2009 | Rudolph | A41D 1/086 |
| | | | 2/269 |
| 7,662,121 B2 | 2/2010 | Zours | |
| 7,670,205 B2 * | 3/2010 | Oyama | C07D 417/12 |
| | | | 450/97 |
| 7,671,388 B2 | 3/2010 | Fujikawa | |
| 7,731,564 B2 | 6/2010 | Sanders | |
| 7,871,388 B2 | 1/2011 | Brown | |
| 7,914,473 B2 | 3/2011 | Josey | |
| 7,922,682 B2 | 4/2011 | Bell | |
| 8,047,893 B2 | 11/2011 | Fenske | |
| 8,083,693 B1 | 12/2011 | McKeon | |
| 8,257,140 B2 * | 9/2012 | Kenny | A41C 3/0035 |
| | | | 450/36 |
| 8,308,670 B2 | 11/2012 | Sandifer | |
| 8,465,341 B2 | 6/2013 | Shashy | |
| 8,516,614 B2 | 8/2013 | Karasina | |
| 8,523,629 B2 | 9/2013 | Pundyk | |
| 8,549,763 B2 * | 10/2013 | Krawchuk | A41B 9/00 |
| | | | 2/243.1 |
| 8,556,840 B2 | 10/2013 | Burke | |
| 8,561,213 B2 * | 10/2013 | Howell | A41B 1/08 |
| | | | 2/2.5 |
| 8,561,214 B2 * | 10/2013 | Turner | A41D 13/05 |
| | | | 2/455 |
| 8,574,027 B2 | 11/2013 | Kipnes | |
| 8,784,351 B2 * | 7/2014 | Dumpson | A41C 1/10 |
| | | | 602/61 |
| 8,795,213 B2 | 8/2014 | Mills | |
| 8,795,215 B2 | 8/2014 | Rossi | |
| 8,887,315 B2 | 11/2014 | Boynton | |
| 8,900,032 B2 | 12/2014 | Punsal | |
| 8,905,956 B2 | 12/2014 | Waeger | |
| 8,910,317 B2 | 12/2014 | Decker | |
| 8,915,765 B2 | 12/2014 | Chayet | |
| 8,926,398 B1 | 1/2015 | Mendeleev | |
| 8,932,236 B1 | 1/2015 | Mckeon | |
| D725,348 S * | 3/2015 | Cutler | D2/731 |
| 9,009,863 B2 | 4/2015 | Decker | |
| 9,027,169 B2 * | 5/2015 | Turner | A41D 13/0506 |
| | | | 2/400 |
| 9,167,854 B2 | 10/2015 | Levian | |
| 9,168,167 B2 | 10/2015 | Brown | |
| 9,226,534 B2 | 1/2016 | Puni | |
| 9,226,845 B2 | 1/2016 | Troncoso | |
| 9,326,553 B1 | 5/2016 | Ross | |
| 9,370,206 B1 | 6/2016 | Ellington | |
| 9,370,440 B2 | 6/2016 | Ingimundarson | |
| 9,414,954 B2 * | 8/2016 | Brown | A41D 13/06 |
| 9,439,459 B2 | 9/2016 | Placanica | |
| 9,445,932 B2 | 9/2016 | Boynton | |
| 9,456,919 B2 | 10/2016 | Pollack | |
| 9,504,280 B2 | 11/2016 | Michael | |
| 9,572,705 B2 | 2/2017 | Ingimundarson | |
| 9,687,378 B1 | 6/2017 | Titen | |
| 9,730,475 B1 | 8/2017 | Tomkoria | |
| 9,743,693 B2 | 8/2017 | Zambelli | |
| 9,883,703 B2 | 2/2018 | Schultz | |
| 9,931,236 B2 | 4/2018 | Williamson | |
| 10,051,897 B2 * | 8/2018 | Freddi | A41D 31/18 |
| 10,201,192 B1 | 2/2019 | Lott | |
| 10,206,436 B1 | 2/2019 | Wooley-Scheiman | |
| 10,213,331 B1 | 2/2019 | Weiler | |
| 10,219,553 B2 * | 3/2019 | Curran | A41D 1/084 |
| 10,226,085 B2 * | 3/2019 | Loyens | A41D 31/185 |
| 10,294,593 B2 * | 5/2019 | Padin | A41C 1/003 |
| 10,398,183 B2 * | 9/2019 | Berns | A41D 27/205 |
| 11,224,258 B2 * | 1/2022 | Berns | A41D 27/207 |
| 2002/0031978 A1 | 3/2002 | Heroff | |
| 2002/0073476 A1 | 6/2002 | Jastrab | |
| 2002/0106970 A1 | 8/2002 | Falla | |
| 2002/0193048 A1 | 12/2002 | Kato | |
| 2004/0058618 A1 | 3/2004 | Yang | |
| 2004/0107479 A1 | 6/2004 | Dicker | |
| 2004/0133959 A1 | 7/2004 | Horii | |
| 2004/0137821 A1 | 7/2004 | Sandroussi | |
| 2004/0143204 A1 | 7/2004 | Salmon | |
| 2004/0221357 A1 * | 11/2004 | Roux | A41D 1/089 |
| | | | 2/69 |
| 2004/0235581 A1 | 11/2004 | Citron | |
| 2004/0244097 A1 | 12/2004 | Kassai | |
| 2004/0255358 A1 * | 12/2004 | Ota | A41D 31/18 |
| | | | 2/69 |
| 2005/0070830 A1 | 3/2005 | Schultz | |
| 2005/0197607 A1 | 9/2005 | Brown | |
| 2005/0229293 A1 * | 10/2005 | Miller | A41D 1/089 |
| | | | 2/403 |
| 2006/0000478 A1 | 1/2006 | Taylor | |
| 2006/0025039 A1 | 2/2006 | Barbour | |
| 2006/0161082 A1 | 7/2006 | Rhee | |
| 2006/0169004 A1 * | 8/2006 | Belluye | A41D 31/18 |
| | | | 66/177 |
| 2006/0194509 A1 | 8/2006 | Patterson | |
| 2006/0230488 A1 * | 10/2006 | Rudolph | A41D 1/086 |
| | | | 2/69 |
| 2006/0277645 A1 * | 12/2006 | Okajima | A41F 3/00 |
| | | | 2/69 |
| 2007/0010768 A1 | 1/2007 | Simanovsky | |
| 2007/0016120 A1 | 1/2007 | Latronica | |
| 2007/0032771 A1 * | 2/2007 | Abed | A61F 13/49006 |
| | | | 604/385.22 |
| 2007/0175005 A1 | 8/2007 | Latronica | |
| 2007/0281586 A1 | 12/2007 | Pritchard | |
| 2008/0000478 A1 | 1/2008 | Matthiessen | |
| 2008/0026676 A1 | 1/2008 | Rothman | |
| 2008/0134409 A1 | 6/2008 | Karasina | |
| 2008/0178369 A1 * | 7/2008 | Kitsch | A41B 9/023 |
| | | | 2/405 |
| 2008/0194179 A1 | 8/2008 | Leung | |
| 2009/0062704 A1 | 3/2009 | Brown | |
| 2009/0075562 A1 | 3/2009 | Lung | |
| 2009/0081924 A1 | 3/2009 | Puyaubreau | |
| 2009/0117826 A1 | 5/2009 | Crouch | |
| 2009/0126084 A1 | 5/2009 | Fenske | |
| 2009/0209172 A1 | 8/2009 | Getz | |
| 2009/0247046 A1 | 10/2009 | Fine | |
| 2009/0258572 A1 | 10/2009 | Chayo | |
| 2009/0259159 A1 | 10/2009 | Bell | |
| 2009/0265830 A1 | 10/2009 | Hendrickson | |
| 2009/0265831 A1 | 10/2009 | Hendrickson | |
| 2009/0270013 A1 | 10/2009 | Clair | |
| 2010/0005569 A1 | 1/2010 | Sanders | |
| 2010/0019227 A1 | 1/2010 | Wasshuber | |
| 2010/0050313 A1 | 3/2010 | Shackelford, Jr. | |
| 2010/0192274 A1 | 8/2010 | Karasina | |
| 2010/0298914 A1 | 11/2010 | Rosenbaum | |
| 2010/0325766 A1 * | 12/2010 | Mackintosh | A41D 31/24 |
| | | | 2/22 |
| 2011/0009793 A1 * | 1/2011 | Lucero | A41D 13/0015 |
| | | | 602/61 |
| 2011/0131697 A1 | 6/2011 | Kawahara | |
| 2011/0213283 A1 | 9/2011 | Brown | |
| 2011/0214216 A1 | 9/2011 | Zarabi | |
| 2011/0237993 A1 | 9/2011 | Kirk | |
| 2011/0271415 A1 * | 11/2011 | Torry | A41D 1/08 |
| | | | 2/23 |
| 2011/0275276 A1 | 11/2011 | Shashy | |
| 2011/0289648 A1 * | 12/2011 | Burke | A41B 9/00 |
| | | | 2/69 |
| 2012/0021669 A1 | 1/2012 | Johnstone | |
| 2012/0040588 A1 | 2/2012 | Steele | |
| 2012/0059297 A1 | 3/2012 | Newkirk | |
| 2012/0078149 A1 | 3/2012 | Azimzadeh | |
| 2012/0122370 A1 | 5/2012 | Heath | |
| 2012/0142252 A1 | 6/2012 | Hopkins | |

(56) References Cited

U.S. PATENT DOCUMENTS

| | | | |
|---|---|---|---|
| 2012/0149277 A1 | 6/2012 | Moses-Jones | |
| 2012/0150085 A1 | 6/2012 | Kayser | |
| 2012/0174282 A1 | 7/2012 | Newton | |
| 2012/0197160 A1 | 8/2012 | Reinhardt | |
| 2012/0244782 A1 | 9/2012 | Pundyk | |
| 2012/0266361 A1* | 10/2012 | Maier | A41D 1/084 2/227 |
| 2012/0316483 A1 | 12/2012 | Waeger | |
| 2012/0330205 A1 | 12/2012 | Liao | |
| 2013/0014311 A1* | 1/2013 | Chapuis | A41D 27/00 2/69 |
| 2013/0025020 A1 | 1/2013 | Miyake | |
| 2013/0045661 A1 | 2/2013 | Armanino | |
| 2013/0047313 A1 | 2/2013 | Windisch | |
| 2013/0053744 A1 | 2/2013 | Convert | |
| 2013/0065486 A1 | 3/2013 | Hansen | |
| 2013/0090521 A1 | 4/2013 | Lau | |
| 2013/0103079 A1 | 4/2013 | Lau | |
| 2013/0115852 A1 | 5/2013 | Blackwell | |
| 2013/0125293 A1* | 5/2013 | Stearns | A41D 1/06 2/227 |
| 2013/0183885 A1 | 7/2013 | Yamazaki | |
| 2013/0211302 A1 | 8/2013 | Brown | |
| 2013/0217302 A1 | 8/2013 | Raj | |
| 2013/0239294 A1* | 9/2013 | Clement | A41D 1/08 2/228 |
| 2013/0296756 A1 | 11/2013 | Troncoso | |
| 2013/0303049 A1 | 11/2013 | Jackson | |
| 2014/0017977 A1 | 1/2014 | Horii | |
| 2014/0024973 A1 | 1/2014 | Pettit | |
| 2014/0047618 A1* | 2/2014 | Robins | A41D 1/084 2/235 |
| 2014/0053322 A1* | 2/2014 | Zamler | A41D 1/084 2/407 |
| 2014/0058307 A1 | 2/2014 | Marshall | |
| 2014/0087625 A1 | 3/2014 | Ironi | |
| 2014/0100501 A1 | 4/2014 | Burke | |
| 2014/0115747 A1* | 5/2014 | Spruill | A41D 13/0015 2/22 |
| 2014/0134922 A1 | 5/2014 | Hearty | |
| 2014/0141692 A1 | 5/2014 | Yuasa | |
| 2014/0221893 A1 | 8/2014 | Modglin | |
| 2014/0227893 A1 | 8/2014 | Howard | |
| 2014/0235139 A1 | 8/2014 | Chayet | |
| 2014/0242876 A1 | 8/2014 | Kitagawa | |
| 2014/0336556 A1 | 11/2014 | Pucik | |
| 2014/0371039 A1 | 12/2014 | Burrell | |
| 2015/0040286 A1 | 2/2015 | Schultz | |
| 2015/0056890 A1 | 2/2015 | Black | |
| 2015/0072591 A1 | 3/2015 | Almog | |
| 2015/0080860 A1 | 3/2015 | Farrell | |
| 2015/0128331 A1* | 5/2015 | Grosse | A41D 31/185 2/400 |
| 2015/0133841 A1 | 5/2015 | Chen | |
| 2015/0257914 A1 | 9/2015 | Pollack | |
| 2016/0015090 A1 | 1/2016 | Mazourik | |
| 2016/0037829 A1 | 2/2016 | Cronin | |
| 2016/0044971 A1 | 2/2016 | Randall | |
| 2016/0058075 A1 | 3/2016 | Dandapure | |
| 2016/0058597 A1 | 3/2016 | Williams | |
| 2016/0081398 A1 | 3/2016 | Tempesta | |
| 2016/0206015 A1 | 7/2016 | Zambelli | |
| 2016/0213071 A1* | 7/2016 | Vornle von Haagenfels | A41D 1/08 |
| 2016/0219947 A1* | 8/2016 | Nhim | A41F 19/00 |
| 2016/0278963 A1 | 9/2016 | Webster | |
| 2016/0316825 A1* | 11/2016 | Cutler | A41D 13/02 |
| 2016/0374405 A1 | 12/2016 | Washington | |
| 2017/0035130 A1 | 2/2017 | Hazzard | |
| 2017/0143048 A1 | 5/2017 | Bucciarelli, III | |
| 2017/0202274 A1 | 7/2017 | Blackwell | |
| 2017/0208873 A1 | 7/2017 | Farneti | |
| 2017/0238634 A1* | 8/2017 | Berns | A41D 1/085 |
| 2017/0238638 A1 | 8/2017 | Flockton | |
| 2017/0252601 A1* | 9/2017 | McKenzie | A63B 23/0205 |
| 2017/0273365 A1 | 9/2017 | Muhlenfeld | |
| 2017/0296359 A1 | 10/2017 | Conway | |
| 2017/0354530 A1 | 12/2017 | Shagdar | |
| 2017/0360118 A1 | 12/2017 | Randall | |
| 2017/0361151 A1* | 12/2017 | Mottern | A41D 13/0015 |
| 2018/0014579 A1 | 1/2018 | Gumlaw | |
| 2018/0132543 A1 | 5/2018 | Schultz | |
| 2018/0249777 A1* | 9/2018 | Turner | A41D 31/02 |
| 2018/0263299 A1* | 9/2018 | Padin | A41B 9/04 |
| 2018/0279694 A1* | 10/2018 | Theno | A41B 9/12 |
| 2018/0325196 A1* | 11/2018 | Miller | D06M 23/16 |
| 2018/0325714 A1 | 11/2018 | Froula | |
| 2019/0037933 A1* | 2/2019 | Mercer | A41D 1/065 |
| 2019/0350281 A1* | 11/2019 | Berns | A41D 27/205 |
| 2020/0170317 A1* | 6/2020 | Johnson | A41D 13/015 |
| 2021/0298369 A1* | 9/2021 | Polstein | A41D 31/305 |

FOREIGN PATENT DOCUMENTS

| | | | |
|---|---|---|---|
| CN | 201048998 | 4/2008 | |
| CN | 201048999 | 4/2008 | |
| CN | 201049000 | 4/2008 | |
| CN | 201049001 | 4/2008 | |
| CN | 201049002 | 4/2008 | |
| CN | 201160505 | 12/2008 | |
| CN | 201316333 | 9/2009 | |
| EP | 3315103 | 5/2018 | |
| JP | 3131863 U | 5/2007 | |
| JP | 2007119994 | 5/2007 | |
| JP | 2008214813 | 9/2008 | |
| JP | 3146561 U | 11/2008 | |
| JP | 2008279065 | 11/2008 | |
| JP | 2011072323 | 4/2011 | |
| JP | 2013112912 | 6/2013 | |
| JP | 2015030924 | 2/2015 | |
| KR | 20140005824 | 1/2014 | |
| WO | 9635400 | 11/1996 | |
| WO | WO-2016086288 A1 * | 6/2016 | A41B 9/12 |
| WO | WO-2018066504 A1 * | 4/2018 | A41D 1/06 |
| WO | WO-2020086330 A1 * | 4/2020 | A41B 17/00 |
| WO | WO-2021153686 A1 * | 8/2021 | |

OTHER PUBLICATIONS

Written Opinion of the International Searching Authority PCT/US2018/041162 Mailed Oct. 30, 2018 4 pages.

Office Action dated Dec. 22, 2020 for U.S. Appl. No. 16/029,567 (pp. 1-16).

Office Action dated Dec. 30, 2020 for U.S. Appl. No. 16/147,639 (pp. 1-13).

Office Action (Non-Final Rejection) dated Sep. 28, 2021 for U.S. Appl. No. 16/845,728 (pp. 1-23).

Office Action (Non-Final Rejection) dated Dec. 8, 2021 for U.S. Appl. no. 16/867,179 (pp. 1-19).

Office Action (Notice of Allowance and Fees Due (PTOL-85)) dated Jun. 3, 2022 for U.S. Appl. No. 16/867,179 (pp. 1-10).

* cited by examiner

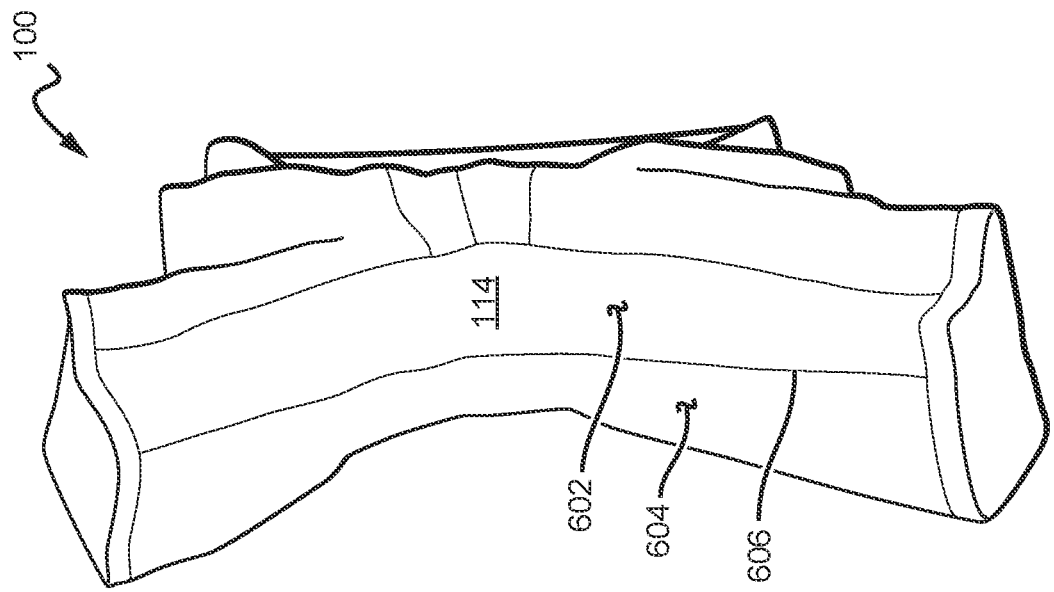
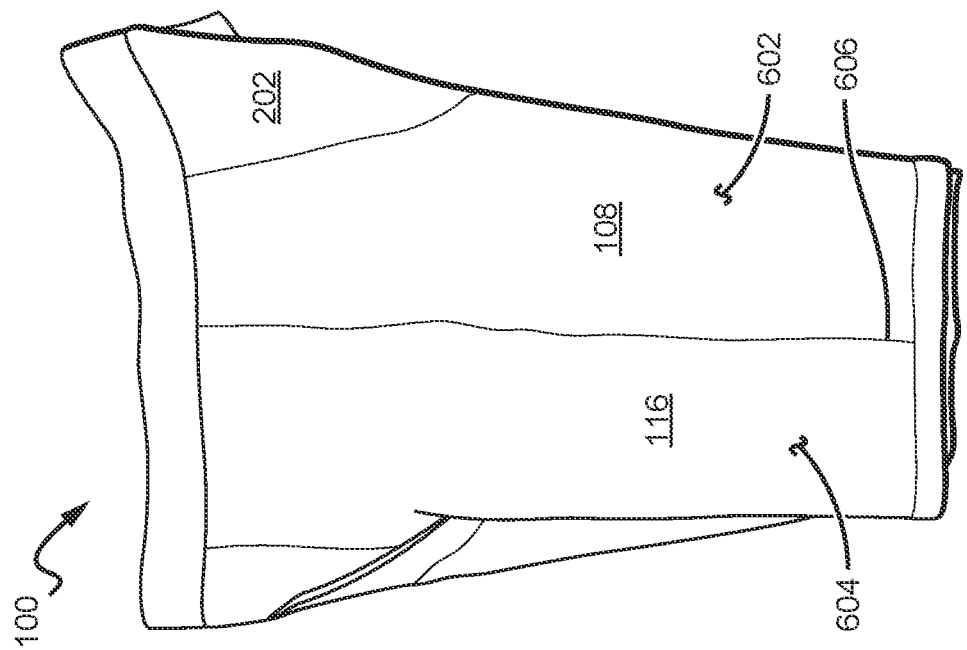

WEARABLE ORTHOPEDIC DEVICE FOR LOWER BODY POSTURE CORRECTION AND IMPROVED ERGONOMICS

RELATED APPLICATION

This application is a continuation-in-part of U.S. patent application Ser. No. 29/714,472, filed on Nov. 22, 2019. This application is also a continuation-in-part of U.S. patent application Ser. No. 29/714,475, filed on Nov. 22, 2019. This application is also a continuation-in-part of U.S. patent application Ser. No. 16/368,588 entitled KINEMATIC BRA FOR POSTURE RECOVERY AND THORACIC MOBILITY filed Mar. 28, 2019, which is a continuation-in-part of U.S. patent application Ser. No. 16/147,639 entitled POSTURE RECOVERY THERAPEUTIC BRA filed Sep. 29, 2018, which is a continuation of U.S. patent application Ser. No. 16/125,453 entitled POSTURE, PERFORMANCE, RECOVERY (PPR) BRA filed Sep. 7, 2018, which is a continuation-in-part application of U.S. patent application Ser. No. 16/057,558 entitled POSTURE, PERFORMANCE, RECOVERY (PPR) BRA filed on Aug. 7, 2018, which is a continuation-in-part application of U.S. patent application Ser. No. 16/029,567 entitled POSTURE, PERFORMANCE, RECOVERY (PPR) BRA filed on Jul. 7, 2018, which claims priority to U.S. Provisional Patent Application No. 62/649,542, entitled POSTURAL RECOVERY BRA, filed Mar. 28, 2018. Each of the applications referred to in this paragraph are hereby incorporated by reference in their entirety as if set forth fully herein.

FIELD OF THE DISCLOSURE

The present disclosure is related to the field of medical devices, especially wearable orthopedic devices for lower body posture correction and improved ergonomics.

BACKGROUND OF THE DISCLOSURE

The importance of good posture and ergonomics is well known throughout the health care industry and work place ergonomics, and generally refers to the proper alignment of the body, specifically, to the relative static and dynamic positioning of the body, spine, pelvis, and its limbs. One important key factor to overall body posture is proper hip alignment, which is often associated with a neutral pelvis. A neutral pelvis is a position of the pelvis where the anterior superior iliac spine (ASIS) is in vertical alignment with the pubic crest. If the ASIS tilts forward in front of the pubic crest, then it creates an anterior pelvic tilt (APT), which can cause unwanted strain and curvature on the spine as well as chronic fatigue on the surrounding muscles and tendons. One tendon in particular that can be affected by APT is the iliotibial band (IT band) that runs along the outside of the upper leg from the ilium to the tibia (i.e., from the hip to the knee). Excess stretching of the IT band caused by APT can lead to inflammation of the IT band, known as IT band syndrome (ITBS).

A common known cause of APT is extended periods in a static seated position, such as sitting in a chair at work all day. Sitting for extended periods of time causes the body to adapt to a seated position. In a seated position, the hip flexor muscles (such as the tensor fasciae latae (TFL) and the adductor muscles) can shorten and the hip extensor muscles (such as the hamstrings and gluteus maximus) can lengthen, causing the pelvis to rotate forward toward the anterior of the body.

One way the body adapts to static and dynamic positioning is through proprioception. Two proprioceptors that play an important role in the flexibility of muscles are the muscle spindles and the golgi tendon organs (GTOs), which work together to regulate muscle stiffness and activation. Muscle spindles sense muscle length while GTOs sense muscle tension. When a muscle spindle senses that its agonist muscle is being stretched too far, it will send an afferent signal to the brain that the muscle needs to contract as a protective mechanism. The brain receives this afferent signal and sends an efferent signal back to the agonist muscle to activate and produce contraction. The muscle spindle can also send an afferent signal to the brain to inhibit an antagonist (i.e., opposing) muscle so that it will relax and not contribute to any further stretching of the agonist muscle. GTOs work opposite of muscle spindles to relax an agonist muscle when there is too much tension. A GTO can sense tension in an agonist muscle either when the muscle is contracted or being stretched. GTOs not only sense tension in the muscle but also the rate of tension. When a muscle is stretched slowly, the GTO will sense the slow rate of tension and temporarily inhibit the muscle spindle so that the muscle can relax, which is what occurs during a static stretch. When the body is in a static position that causes stretch on the muscles, the muscle spindles and GTOs begin to adapt to new resting positions such that they will only send signals to the brain under circumstances that deviate from the adapted muscle lengths and tensions.

When the body is in a seated position, the hip flexors shorten while the hip extensors lengthen. Although the hip extensors are being lengthened, the slow rate of stretching causes the GTO to inhibit the muscle spindle and allow the hip flexors to relax. During an extended period of static sitting, the muscle spindles begin to adjust their sensitivities such that their perception of the hip flexors becomes shorter than normal and their perception of the hip extensors becomes longer than normal. When the body stands back up, the bones and tendons (e.g., pelvis and IT band) attempt to return to a normal position, but this causes a stretch on what the muscle spindles perceive the adapted lengths of the hip flexors to be. Sensing a lengthening in the hip flexors, the muscle spindles send afferent signals to the brain to activate the hip flexors and inhibit the hip extensors, which causes the pelvis to tilt forward toward the anterior hip flexors and away from the posterior hip extensors.

A seated position can also shorten the adductor muscles and cause internal rotation of the femurs. When the femurs rotate internally, the femoral head pushes the pubic rami at the bottom of the pelvis backwards and the sacrum upwards, further tilting the pelvis anteriorly.

In addition to pelvic tilt, the shortening of the hip flexors and lengthening of the hip extensors also pulls the IT band in favor of its surrounding hip flexors such as the TFL and away from its surrounding hip extensors such as the hamstrings and gluteus maximus, which can cause unwanted tension and inflammation of the IT band. As such, APT has been associated with ITBS in addition to other postural related conditions.

Certain devices have attempted to correct APT by providing support to weak hip extensor and surrounding muscles to help the body achieve a neutral pelvis. One such device is disclosed in U.S. Pat. No. 7,670,205, explaining that "provision of a support on the piriform muscle leads to a large posture correction effect, and when it is used in combination with a support on the external oblique muscle, better effects can be expected." However, providing support to weak muscles is merely a short fix for when the device is worn and does not offer an effective long-term solution that ultimately trains the body to stand in proper alignment even without the device. Other devices such as the one disclosed in U.S. Pat. No. 9,414,954 comprise numerous bulky and restricting straps that forcibly twist the body into alignment and require manual adjustment.

Dynamic positioning such as running, jumping, golfing, or athletic activity is also benefited by proprioceptive training. During dynamic movement, the GTOs may sense a much higher rate of tension than during static positioning, so they do not inhibit the muscle spindles in the same way described above. Muscle spindles may exhibit a dynamic response to stretch by increasing afferent firing rates to contract the stretched muscles, which can be counterproductive to the intended movement. For example, if the adductors are told to contract when they are being stretched by a dynamic movement, then this can cause internal rotation of the femurs, closing the hips.

Accordingly, there exists a need in the art for a simple device that can be comfortably worn as normal clothing or under normal clothing (for example, at work, during athletic activities, while training, during rehabilitation, for muscle recovery, or on a road trip) that trains the body to proprioceptively achieve better posture, a neutral pelvis, and less stress on the IT band. Accordingly, the present disclosure is aimed at solving these and other problems discussed below.

SUMMARY OF THE DISCLOSURE

Certain embodiments of the present disclosure relate to wearable orthopedic devices for lower body posture correction. More specifically, certain embodiments are directed at men's and women's posture correction shorts. In some embodiments, the orthopedic devices have various carefully positioned panels with variable tensions to target certain areas of the body.

In some embodiments, the device targets areas of the body known to contribute to APT and ITBS by adjusting the sensitivities of proprioceptors such as muscle spindles and GTOs. Certain panels of the device may exert increased levels of tension along the IT band to help prevent it from being stretched by surrounding muscles. Other panels may exert increased levels of tension along the inseam to help prevent internal rotation of the femurs.

It is an object of embodiments of the present disclosure to reduce excessive strain on a wearer's IT band.

It is another object of embodiments of the present disclosure to reduce internal rotation of a wearer's femurs.

It is yet another object of embodiments of the present disclosure to correct a wearer's posture by training the wearer's muscles and proprioceptors.

These and other further features and advantages provided in this disclosure would be apparent to those skilled in the art from the following detailed description, taken together with the accompanying drawings.

BRIEF DESCRIPTION OF THE DRAWINGS

FIG. 9 is a left view of the interior of an orthopedic device according to one embodiment of the disclosure.

FIG. 10 is a bottom view of the interior of an orthopedic device according to one embodiment of the disclosure.

DETAILED DESCRIPTION OF THE DISCLOSURE

Figure 2:
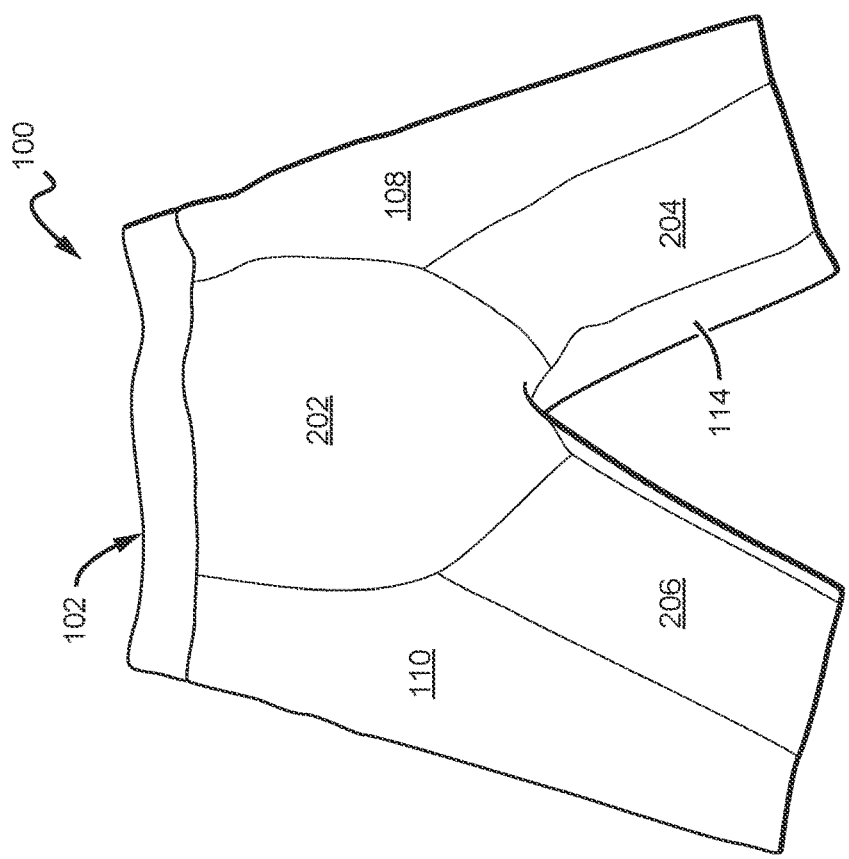
FIG. 2 is a back view of the exterior of an orthopedic device according to one embodiment of the disclosure.

Throughout this disclosure, the embodiments illustrated should be considered as exemplars, rather than as limitations on the present disclosure. As used herein, the term "invention," "device," "apparatus," "method," "disclosure," "present invention," "present device," "present apparatus," "present method," or "present disclosure" refers to any one of the embodiments of the disclosure described herein, and any equivalents. Furthermore, reference to various features of the "invention," "device," "apparatus," "method," "disclosure," "present invention," "present device," "present apparatus," "present method," or "present disclosure" throughout this document does not mean that all claimed embodiments or methods must include the reference features.

It is also understood that when an element or feature is referred to as being "on" or "adjacent" to another element or feature, it can be directly on or adjacent the other element or feature or intervening elements or features may also be present. In contrast, when an element is referred to as being "directly on" or extending "directly onto" another element, there are no intervening elements present. Additionally, it is understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Furthermore, relative terms such as "inner," "outer," "upper," "top," "above," "lower," "bottom," "beneath," "below," and similar terms, may be used herein to describe a relationship of one element to another. Terms such as "higher," "lower," "wider," "narrower," and similar terms, may be used herein to describe angular relationships. It is understood that these terms are intended to encompass different orientations of the elements or system in addition to the orientation depicted in the figures.

Although the terms first, second, third, etc., may be used herein to describe various elements, components, regions, and/or sections, these elements, components, regions, and/or sections should not be limited by these terms. These terms are only used to distinguish one element, component, region, or section from another. Thus, unless expressly stated otherwise, a first element, component, region, or section discussed below could be termed a second element, component, region, or section without departing from the teachings of the present disclosure. As used herein, the term "and/or" includes any and all combinations of one or more of the associated list items.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. For example, when the present specification refers to "an" assembly, it is understood that this language encompasses a single assembly or a plurality or array of assemblies. It is further understood that the terms "comprises," "comprising," "includes," and/or "including" when used herein, specify the presence of stated features, integers, steps, operations, elements, and/or components, but do not preclude the presence or addition of one or more other features, integers, steps, operations, elements, components, and/or groups thereof.

Embodiments as described in the present disclosure can be described herein with reference to view illustrations, some of which are schematic in nature. As such, the actual thickness of elements can be different, and variations from the shapes of the some of the illustrations as a result, for example, of manufacturing techniques and/or tolerances are expected. Thus, the elements illustrated in the some of the figures are schematic in nature and their shapes are not intended to illustrate the precise shape of a region and are not intended to limit the scope of the disclosure.

Figure 1:
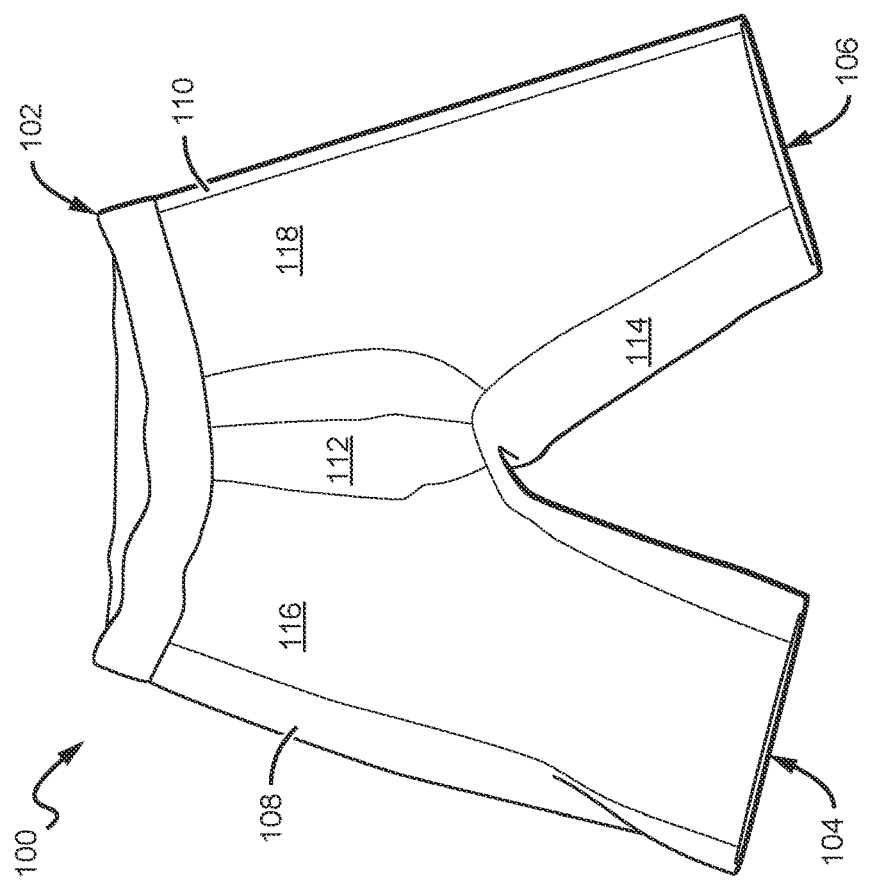
FIG. 1 is a front view of the exterior of an orthopedic device according to one embodiment of the disclosure.
Figure 4:
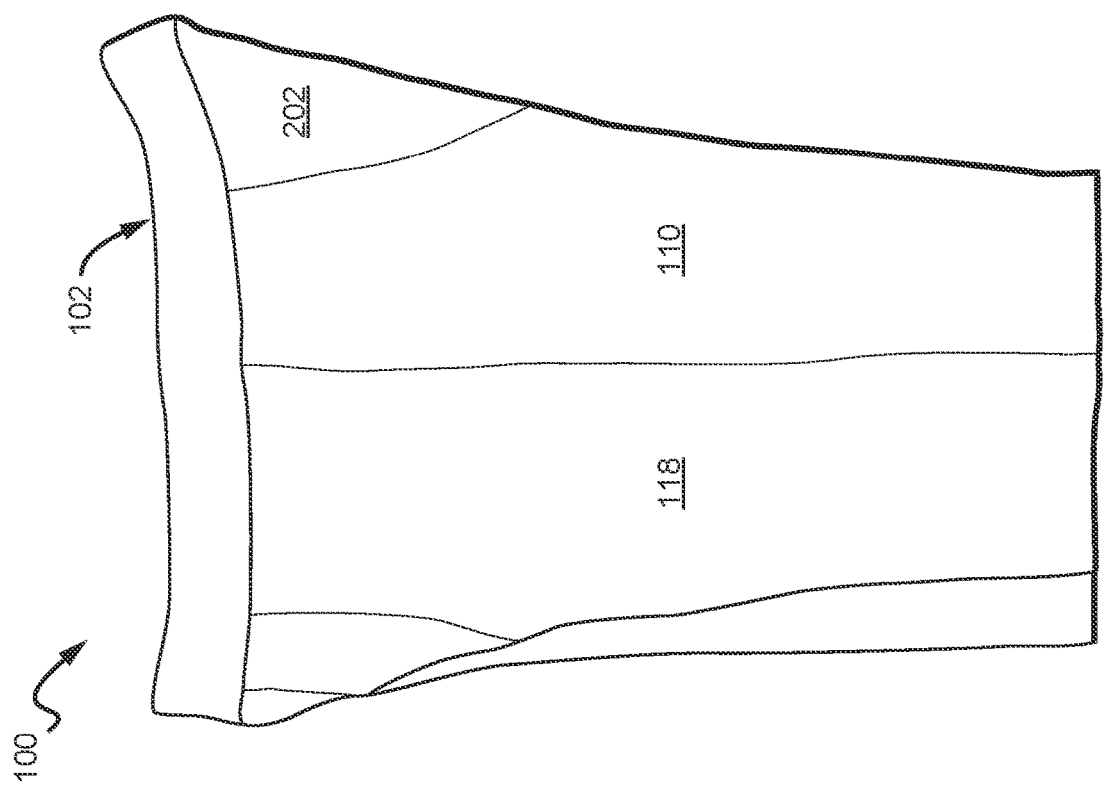
FIG. 4 is a left view of the exterior of an orthopedic device according to one embodiment of the disclosure.
Figure 3:
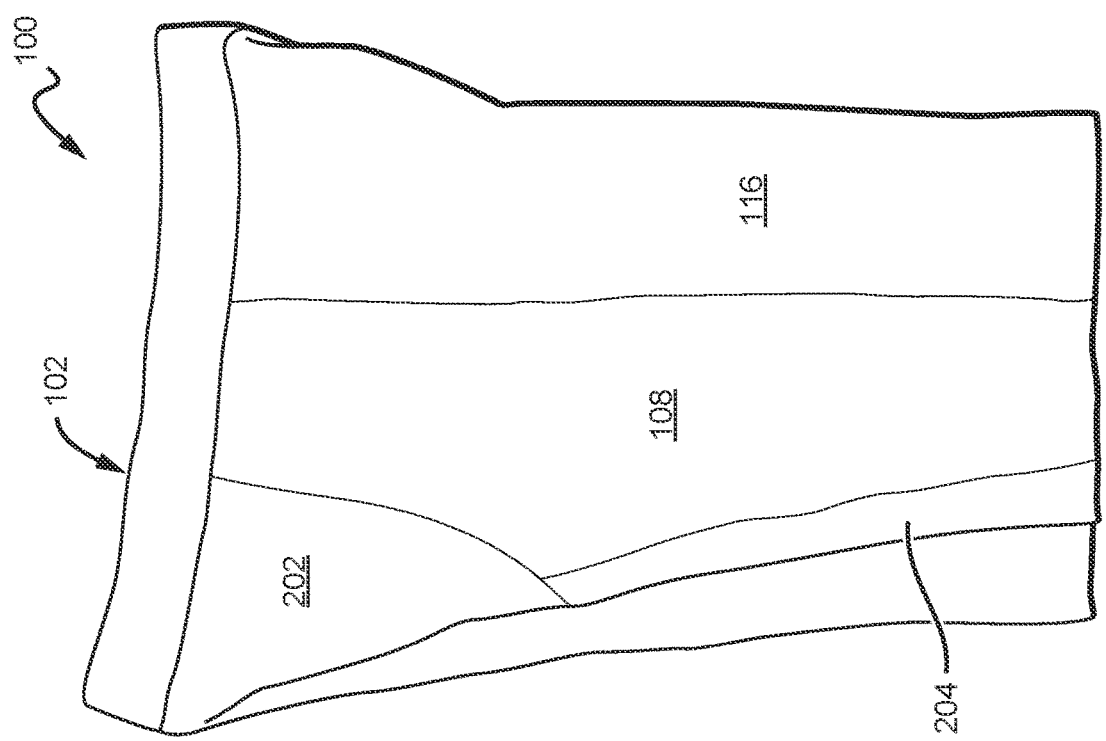
FIG. 3 is a right view of the exterior of an orthopedic device according to one embodiment of the disclosure.
Figure 5:
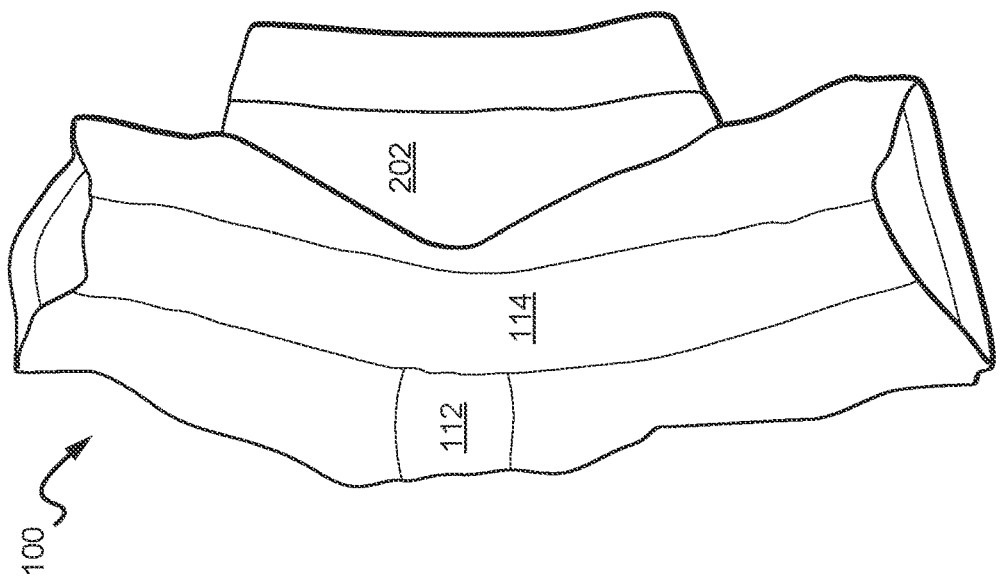
FIG. 5 is a bottom view of the exterior of an orthopedic device according to one embodiment of the disclosure.

FIGS. 1-5 show various views of the exterior of an orthopedic device 100 according to one embodiment of the disclosure. As shown, device 100 is a pair of men's posture correction shorts. In one embodiment, device 100 comprises a waistband 102, right and left legs 104, 106, and a series of panels. As shown in FIGS. 1-5, the panels may include: a right side panel 108 that runs vertically from the right side of waistband 102 to the bottom of the right side of right leg 104; a left side panel 110 that runs vertically from the left side of waistband 102 to the bottom of the left side of left leg 106; a crotch panel 112 centered on the anterior of device 100; a seat panel 202 centered on the posterior of device 100; an inseam panel 114 running along the bottom of device 100; right and left front panels 116, 118 on the anterior of the device; and right and left back panels 204, 206 on the posterior of the device.

In the embodiment shown in FIGS. 1-5, crotch panel 112 is directly connected to waistband 102 along the front and seat panel 202 is directly connected to waistband 102 along the back. Seat panel 202 is also directly connected to and runs between right and left side panels 108, 110. Inseam panel 114 runs along the bottom of device 100 from the bottom of the left side of right leg 104 to the bottom of the right side of left leg 106 and directly connects between crotch panel 112, right and left front panels 116, 118, seat panel 202, and right and left back panels 204, 206. Right and left front panels 116, 118 are on the anterior of device 100 and are directly connected to waistband 102 with right front panel 116 connected along waistband 102 from crotch panel 112 to right side panel 108 and left front panel 118 connected along waistband 102 from crotch panel 112 to left side panel 110. Right and left front panels 116, 118 also extend to the bottom of right and left legs 104, 106, respectively. Right and left back panels 204, 206 are on the posterior of device 100 and are directly connected at the top to seat panel 202. Right back panel 204 is directly connected at the right to right side panel 108 and at the left to inseam panel 114. Left back panel 206 is directly connected at the left to left side panel 110 and at the right to inseam panel 114.

Figure 6:
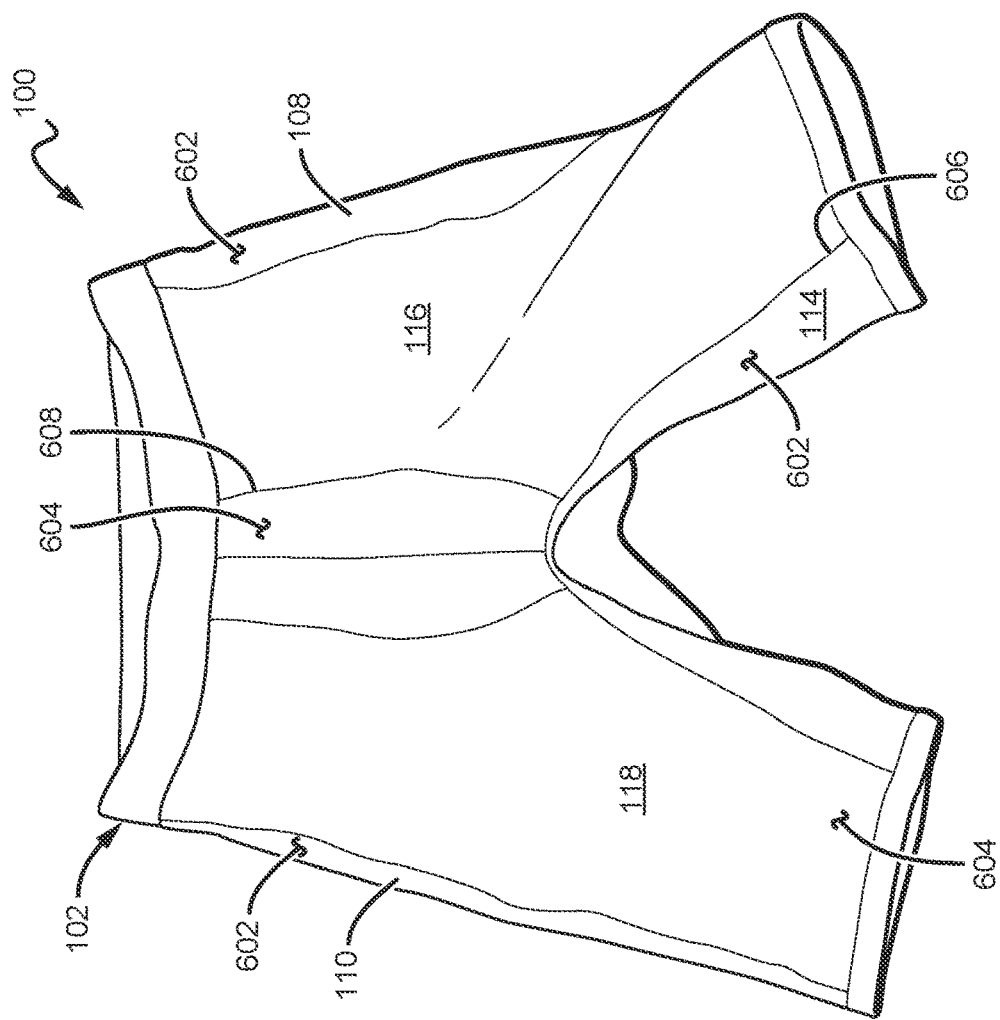
FIG. 6 is a front view of the interior of an orthopedic device according to one embodiment of the disclosure.
Figure 8:
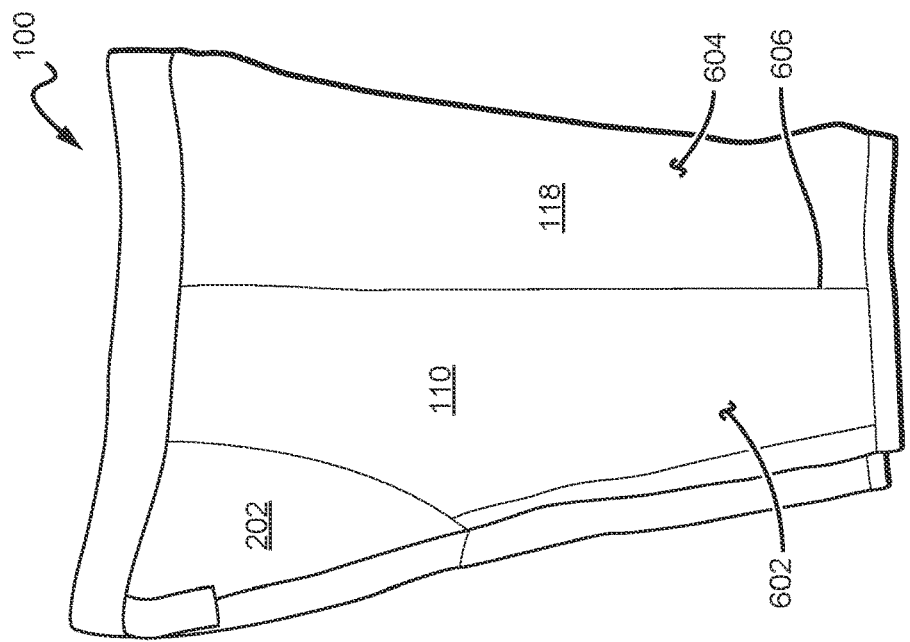
FIG. 8 is a right view of the interior of an orthopedic device according to one embodiment of the disclosure.
Figure 7:
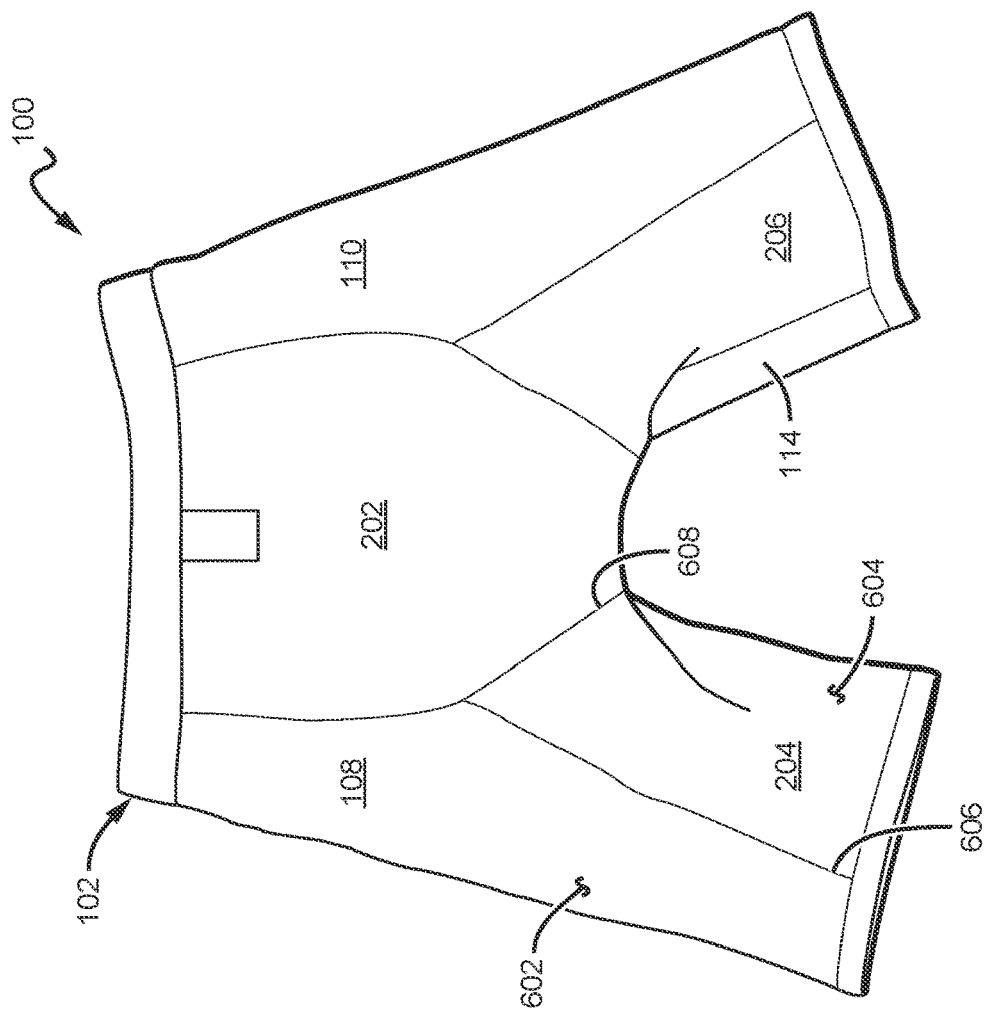
FIG. 7 is a back view of the interior of an orthopedic device according to one embodiment of the disclosure.

FIGS. 6-10 show various views of the interior of device 100 according to one embodiment of the disclosure. As shown in FIGS. 6-10, right side panel 108, left side panel 110, and inseam panel 114 may comprise a double-layer fabric 602 with an interior fabric and an exterior fabric, while crotch panel 112, seat panel 202, right front panel 116, left front panel 118, right back panel 204, and left back panel 206 may comprise a single-layer fabric 604. In certain preferred embodiments, the interior fabric of double-layer fabric 602 comprises a mesh material. These embodiments allow for crotch panel 112, seat panel 202, right front panel 116, left front panel 118, right back panel 204, and left back panel 206 to have a greater elasticity than right side panel 108, left side panel 110, and inseam panel 114. Accordingly, each connection along an edge of right side panel 108, left side panel 110, and inseam panel 114 may comprise a first stitch 606 that is heavier than a second stitch 608 provided along each connection not along one of these edges in order to better attach the panels that comprise additional and less elastic fabrics. In some embodiments, first stitch 606 is a flat lock stitch.

In the embodiment of FIGS. 1-10, device 100 is carefully constructed such that the various components of device 100, including the waistband, panels, fabrics, and stitching, are advantageously positioned for optimal proprioceptive posture training and correction. For example, the double-layer fabric construction of right side panel 108 and left side panel 110 is specifically targeted at providing increased tension along the IT bands. Providing tension along the IT bands helps the surrounding muscles resist lengthening and shortening and remain at a normal length, which prevents the muscle spindles and GTOs from adapting to abnormal positions. Thus, when the body begins to stand, it does not feel a proprioceptive need to contract the hip flexors and relax the hip extensors because it will perceive these muscles to be at a normal length. Without hip flexor contraction, the IT band is also not stretched and is able to maintain a normal position. Likewise, inseam panel 114 provides tension near the adductors so that they will resist shortening and internally rotating the femurs. This, too, will help prevent anterior tilting of the pelvis by keeping the pubic rami in proper alignment.

In addition to working prophylactically to prevent APT, device 100 can also work therapeutically to retrain the body once it is already in APT. If the hip flexors have already been shortened from long periods of sitting, right side panel 108, left side panel 110, and inseam panel 114 will provide tension to pull the hip flexors such as the TFL and adductors back into a normal length. This will cause the body's proprioception to work the same as described above, but now in favor of a neutral pelvis. When the body is already out of alignment, device 100 will create a static stretch on the hip flexors, causing the GTOs to inhibit the muscle spindles and relax the hip flexors. This will, in turn, cause the muscle spindles to readjust to a lengthened position of the hip flexors so that when the body is in a standing position, the muscle spindles will not perceive a need to contract these muscles and pull the pelvis forward. In this way, the body's proprioception is being retrained to perceive a neutral pelvis position as normal again. Retraining the body's proprioception provides lasting effects that can remain even when device 100 is not worn.

Device 100 can also help with dynamic positioning such as running or athletic activity. By maintaining the normal lengths of certain muscles like the adductors, the muscle spindles will not feel a lengthening and tell the body to contract. This can be beneficial, for example, by allowing the hips to open up without internal rotation by the femurs.

Figure 12:
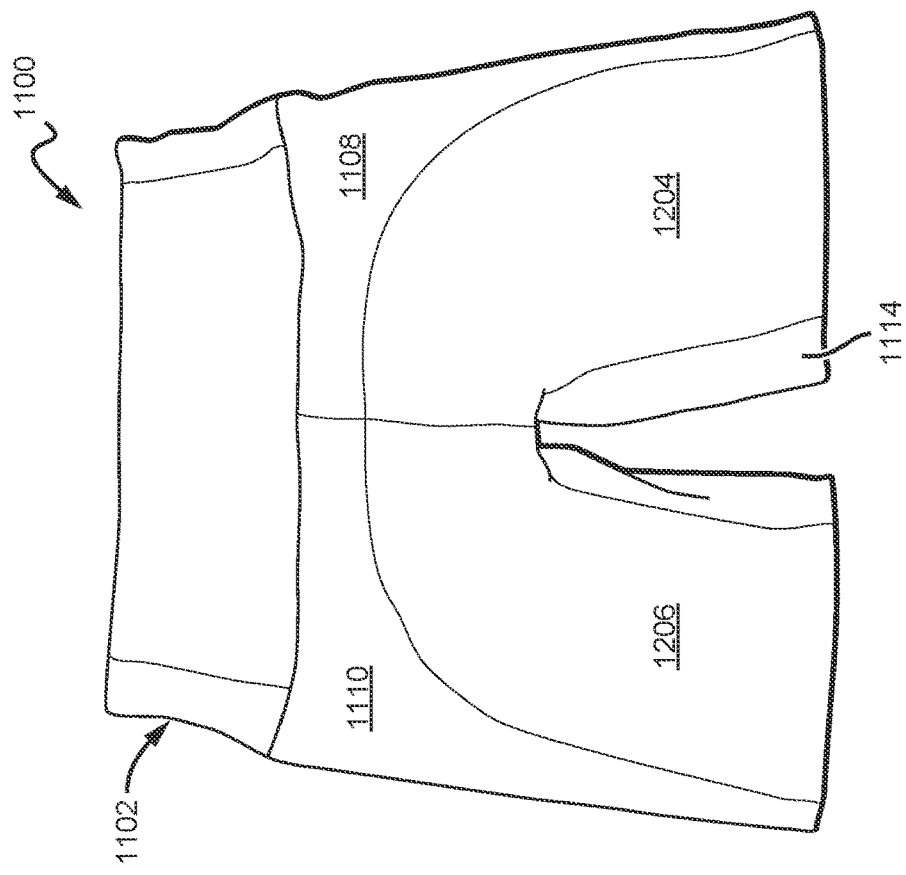
FIG. 12 is a back view of the exterior of an orthopedic device according to another embodiment of the disclosure.
Figure 11:
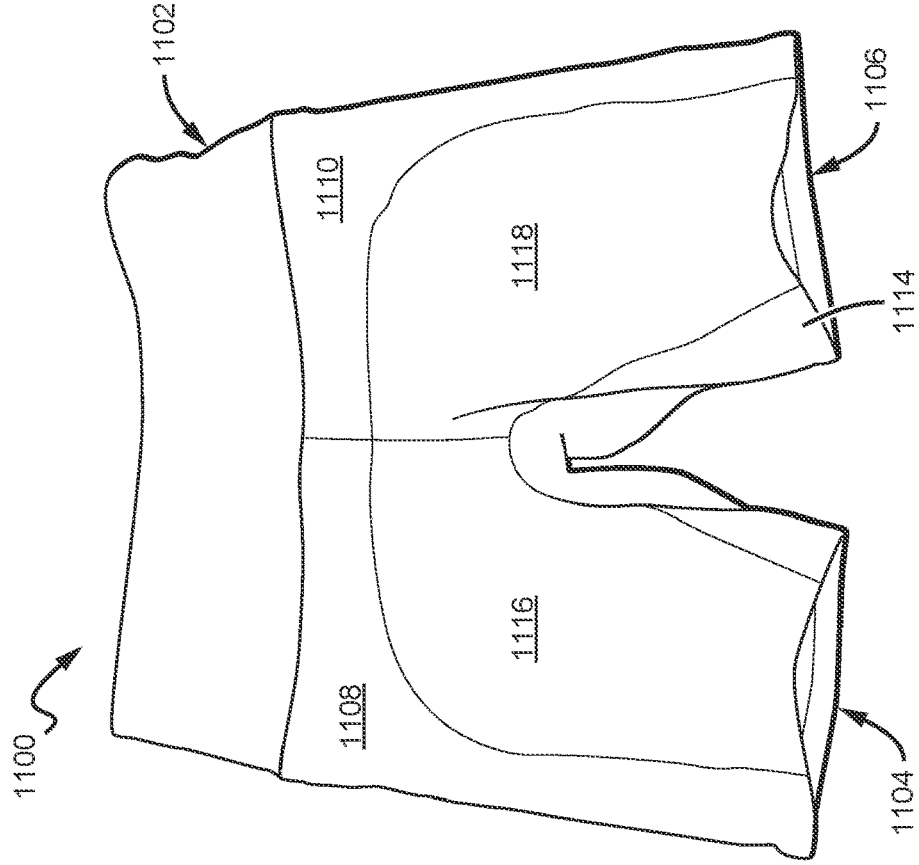
FIG. 11 is a front view of the exterior of an orthopedic device according to another embodiment of the disclosure.
Figure 14:
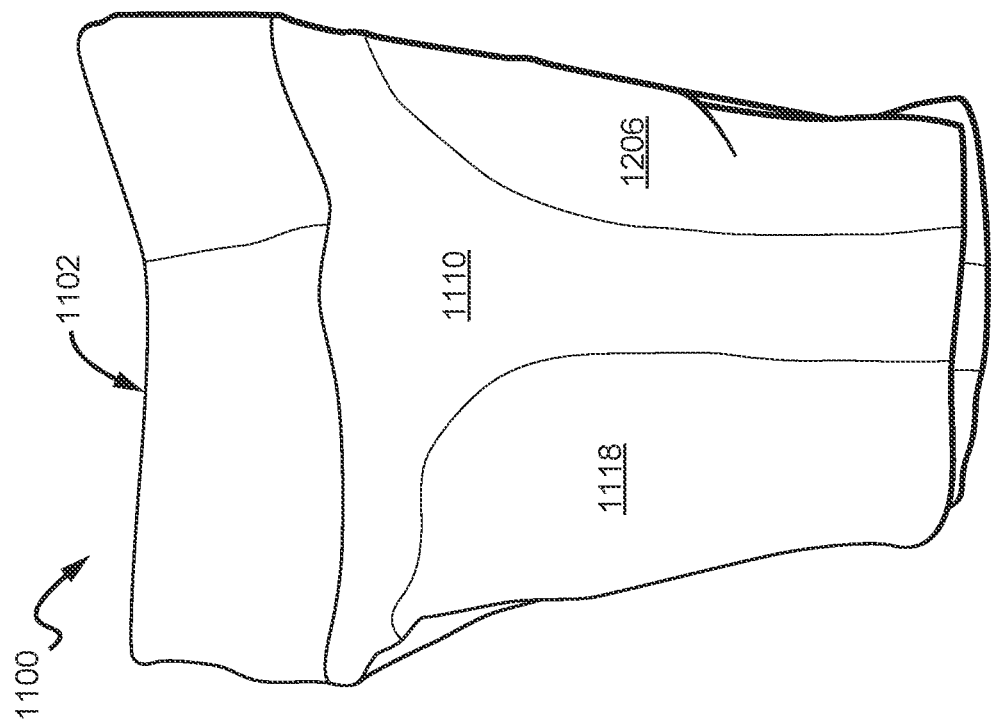
FIG. 14 is a left view of the exterior of an orthopedic device according to another embodiment of the disclosure.
Figure 13:
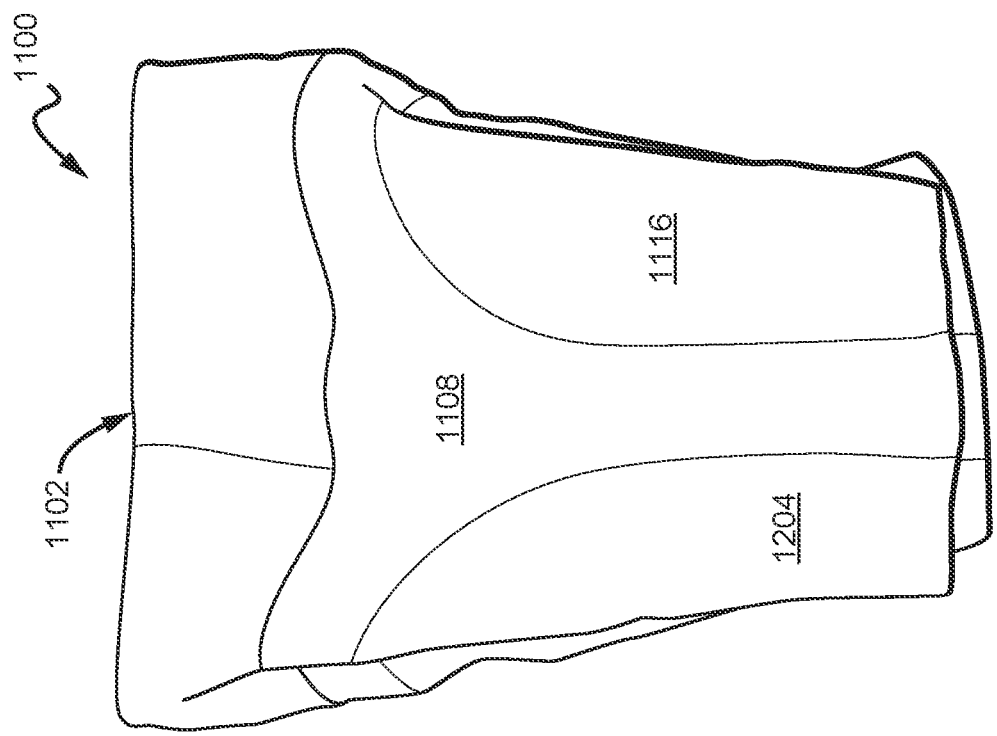
FIG. 13 is a right view of the exterior of an orthopedic device according to another embodiment of the disclosure.
Figure 15:
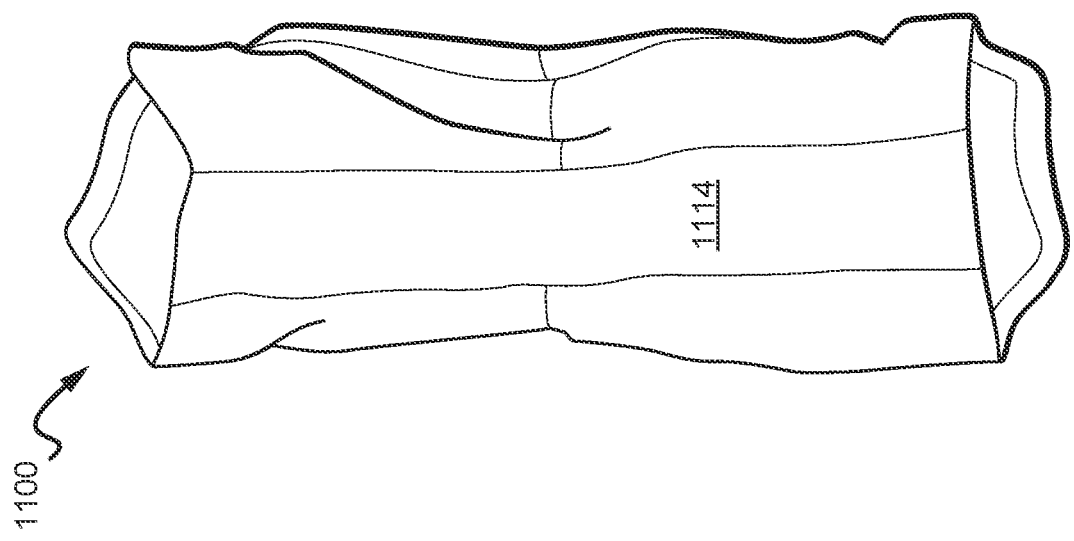
FIG. 15 is a bottom view of the exterior of an orthopedic device according to another embodiment of the disclosure.

FIGS. 11-15 show various views of the exterior of an orthopedic device 1100 according to another embodiment of the disclosure. As shown, device 1100 is a pair of women's posture correction shorts. In the embodiment shown, device 100 comprises a waistband 1102, right and left legs 1104, 1106, and a series of panels. As shown in FIGS. 11-15, the panels may include: a right side panel 1108 that runs vertically from the bottom of the right side of right leg 1104 to the right side of waistband 1102 and curves to extend horizontally along waistband 1102 around the anterior and posterior of device 1100; a left side panel 1110 that runs vertically from the bottom of the left side of left leg 1106 to the left side of waistband 1102 curves to extend horizontally along waistband 1102 around the anterior and posterior of device 1100 to connect with right side panel 1108 at the center of the anterior and posterior of device 1100 below waistband 1102; an inseam panel 1114 running along the bottom of device 1100; right and left front panels 1116, 1118 on the anterior of the device; and right and left back panels 1204, 1206 on the posterior of the device.

In the embodiment shown in FIGS. 11-15, inseam panel 1114 runs along the bottom of device 1100 from the bottom of the left side of right leg 1104 to the bottom of the right side of left leg 1106 and directly connects between right and left front panels 1116, 1118 and right and left back panels 1204, 1206. Right and left front panels 1116, 1118 are directly connected to the anterior of right and left side panels 1108, 1110, respectively, and extend to the bottoms of the front sides of right and left legs 1104, 1106, respectively. Right and left back panels 1204, 1206 are directly connected to the posterior of right and left side panels 1108, 1110, respectively, and extend to the bottoms of the back sides of right and left legs 1104, 1106, respectively.

Figure 16:
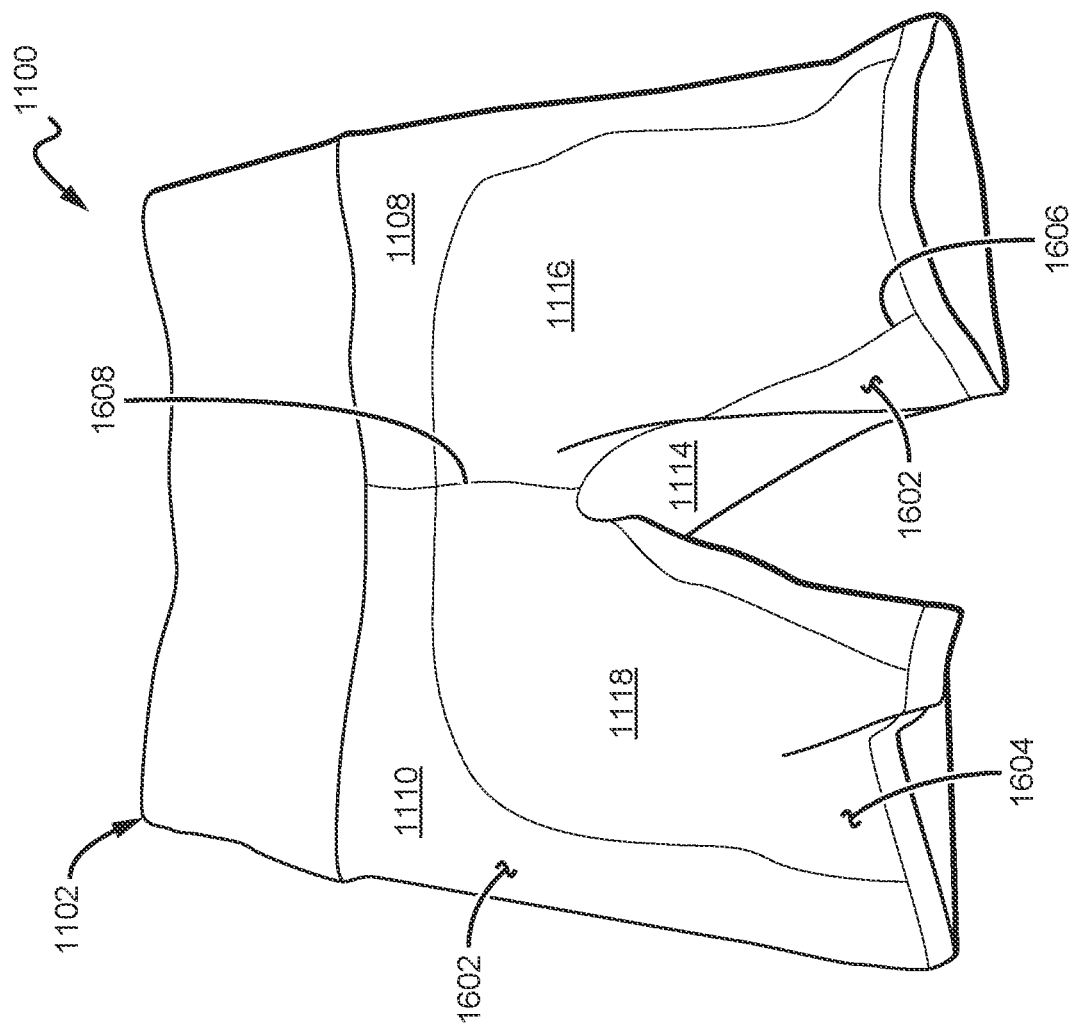
FIG. 16 is a front view of the interior of an orthopedic device according to another embodiment of the disclosure.
Figure 18:
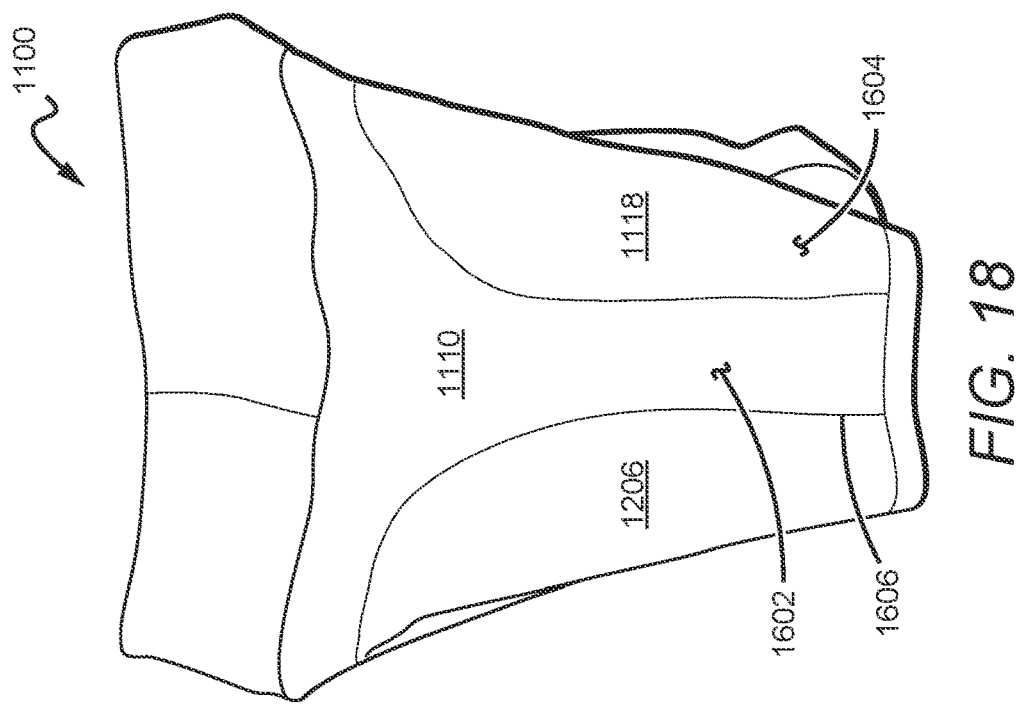
FIG. 18 is a right view of the interior of an orthopedic device according to another embodiment of the disclosure.
Figure 17:
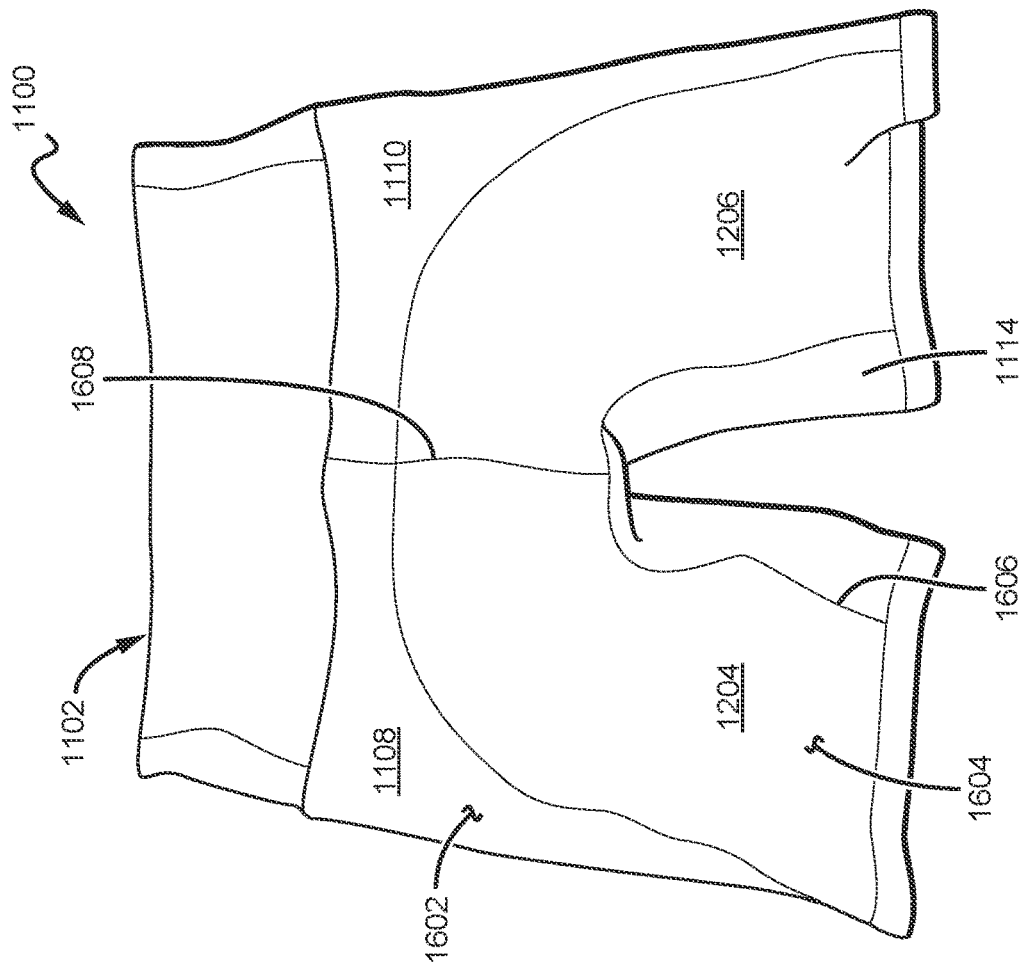
FIG. 17 is a back view of the interior of an orthopedic device according to another embodiment of the disclosure.
Figure 20:
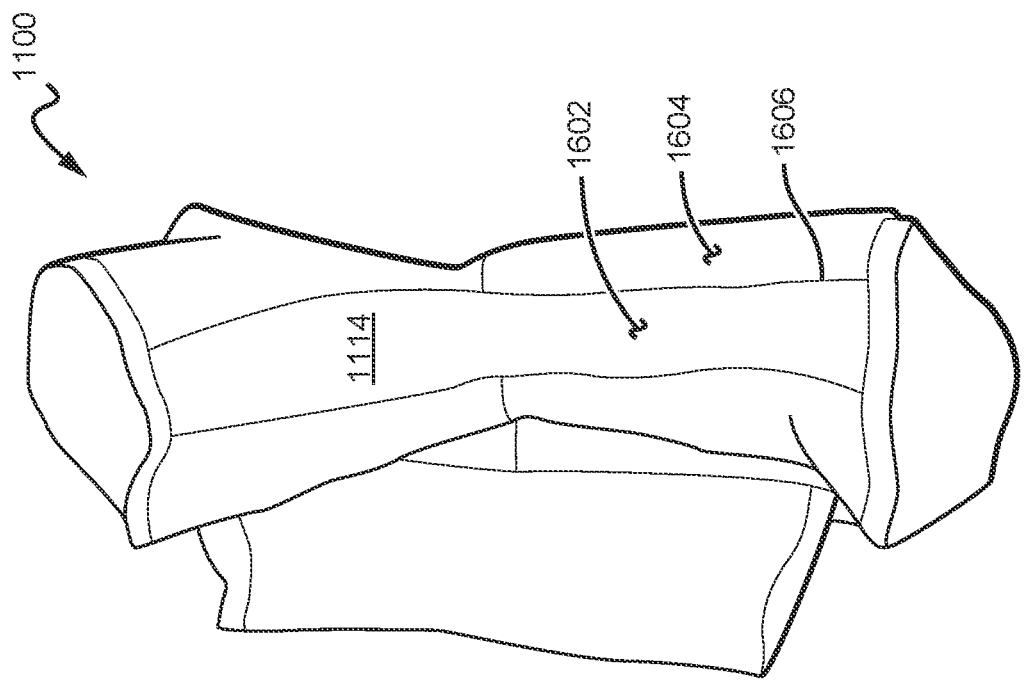
FIG. 20 is a bottom view of the interior of an orthopedic device according to another embodiment of the disclosure.
Figure 19:
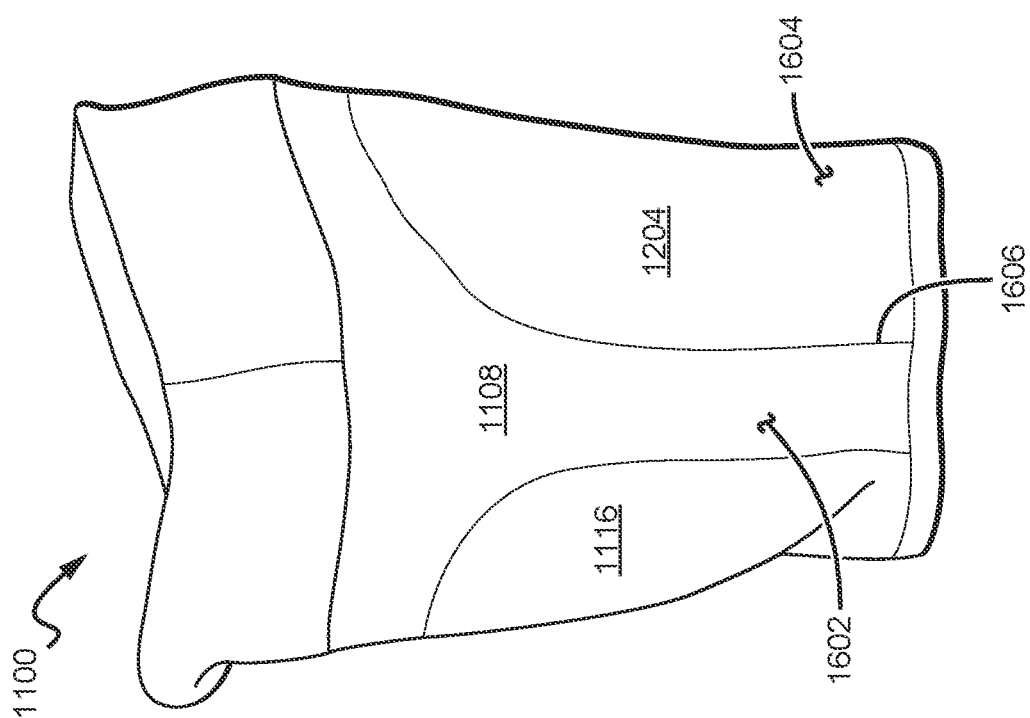
FIG. 19 is a left view of the interior of an orthopedic device according to another embodiment of the disclosure.

FIGS. 16-20 show various views of the interior of device 100 according to one embodiment of the disclosure. As shown in FIGS. 16-20, right side panel 1108, left side panel 1110, and inseam panel 1114 may comprise a double-layer fabric 1602 with an interior fabric and an exterior fabric, while right front panel 1116, left front panel 1118, right back panel 1204, and left back panel 1206 may comprise a single-layer fabric 1604. In certain preferred embodiments, the interior fabric of double-layer fabric 1602 comprises a mesh material. These embodiments allow for right front panel 1116, left front panel 1118, right back panel 1204, and left back panel 1206 to have a greater elasticity than right side panel 1108, left side panel 1110, and inseam panel 1114. Accordingly, each connection along an edge of right side panel 1108, left side panel 1110, and inseam panel 1114 may comprise a first stitch 1606 that is heavier than a second stitch 1608 provided along each connection not along one of these edges in order to better attach the panels that comprise additional and less elastic fabrics. In some embodiments, first stitch 1606 is a flat lock stitch.

It is understood that embodiments presented herein are meant to be exemplary. Embodiments of the present disclosure can comprise any combination or compatible features shown in the various figures, and these embodiments should not be limited to those expressly illustrated and discussed.

Although the present disclosure has been described in detail with reference to certain configurations thereof, other versions are possible. Further, none of the elements or features discussed herein should be construed as necessary, critical, or essential for any particular embodiment of the present disclosure. Therefore, the spirit and scope of the disclosure should not be limited to the versions described above. The foregoing is intended to cover all modifications and alternative constructions falling within the spirit and scope of the disclosure as expressed in the appended claims, wherein no portion of the disclosure is intended, expressly or implicitly, to be dedicated to the public domain if not set forth in the claims.

What is claimed is:

1. A wearable orthopedic device, comprising:
  a waistband;
  a right leg comprising a right side panel, a right front panel, and a right back panel;
  a left leg comprising a left side panel, a left front panel, and a left back panel;
  said right side panel extending vertically from a right side of said waistband to a bottom of a right side of said right leg;
  said left side panel extending vertically from a left side of said waistband to a bottom of a left side of said left leg;
  a crotch panel on an anterior of said device connected along a center front portion of said waistband;
  a seat panel on a posterior of said device connected along a back portion of said waistband from said right side panel to said left side panel;
  an inseam panel extending along a bottom of said device from a bottom of a left side of said right leg to a bottom of a right side of said left leg, said inseam panel connected between said crotch panel and said seat panel;
  said right front panel on the anterior of said device connected along a right front portion of said waistband from said crotch panel to said right side panel and connected to a right side of said inseam panel, said right front panel extending to a bottom of a front side of said right leg;
  said left front panel on the anterior of said device connected along a left front portion of said waistband from said crotch panel to said left side panel and connected to a left side of said inseam panel, said left front panel extending to a bottom of a front side of said left leg;
  said right back panel on the posterior of said device connected to said seat panel at a top edge, said right side panel at a right edge, and said inseam panel at a left edge;
  said left back panel on the posterior of said device connected to said seat panel at a top edge, said left side panel at a left edge, and said inseam panel at a right edge,
  wherein said right side panel, said left side panel, and said inseam panel comprise a double-layer fabric including an interior fabric and an exterior fabric, said interior fabric comprising a mesh material,
  wherein said crotch panel, said seat panel, said right front panel, said left front panel, said right back panel, and said left back panel comprise a single-layer fabric and wherein said crotch panel, said seat panel, said right front panel, said left front panel, said right back panel, and said left back panel have a greater elasticity than said right side panel, said left side panel, and said inseam panel, wherein seams along edges of said right side panel, said left side panel, and said inseam panel to other portions of said device comprise a first stitch type, and seams not along an edge of said right side panel, said left side panel, and said inseam panel comprise a second stitch type, wherein said first stitch type comprises a higher thread density than said second stitch type.

2. The device of claim 1, wherein said double-layer fabric on said right side panel and said left side panel is configured to reduce stretch on a wearer's IT bands.

3. The device of claim 1, wherein said double-layer fabric on said inseam panel is configured to reduce internal rotation of a wearer's femurs.

4. The device of claim 1, wherein said first stitch type is a flat-lock stitch.

5. A wearable orthopedic device, comprising:
a waistband;
a right leg comprising a right side panel, a right front panel, and a right back panel;
a left leg comprising a left side panel, a left front panel, and a left back panel;
an inseam panel;
a crotch panel; and
a seat panel, and
wherein said crotch panel, said seat panel, said right front panel, said left front panel, said right back panel, and said left back panel comprise a single-layer fabric, said right side panel, said left side panel, and said inseam panel comprise a double-layer fabric comprising an interior fabric and an exterior fabric, wherein said right side panel extends vertically from a right side of said waistband to a bottom of a right side of said right leg, wherein said left side panel extends vertically from a left side of said waistband to a bottom of a left side of said left leg, and wherein said single-layer fabric has a greater elasticity than said double-layer fabric and is configured to reduce stretch on a wearer's IT bands, and wherein seams along edges of said right side panel, said left side panel, and said inseam panel to other portions of said device comprise a first stitch type, and seams not along an edge of said right side panel, said left side panel, and said inseam panel comprise a second stitch type, wherein said first stitch type comprises a higher thread density than said second stitch type.

6. The device of claim 5 wherein said crotch panel is located on the anterior of said device and connected along a center front portion of said waistband.

7. The device of claim 6 wherein said seat panel is located on a posterior of said device and connected along a back portion of said waistband from said right side panel to said left side panel.

8. The device of claim 7 wherein said inseam panel extends along a bottom of said device from a bottom of a left side of said right leg to a bottom of a right side of said left leg, said inseam panel directly connected between said crotch panel and said seat panel.

9. The device of claim 7 wherein said right front panel is on the anterior of said device directly connected along a right front portion of said waistband from said crotch panel to said right side panel and directly connected to a right side of said inseam panel, said right front panel extending to a bottom of a front side of said right leg, and wherein said left front panel is on the anterior of said device directly connected along a left front portion of said waistband from said crotch panel to said left side panel and directly connected to a left side of said inseam panel, said left front panel extending to a bottom of a front side of said left leg.

10. The device of claim 7 wherein said right back panel is on the posterior of said device directly connected to said seat panel at a top edge, said right side panel at a right edge, and said inseam panel at a left edge, and wherein said left back panel is on the posterior of said device directly connected to said seat panel at a top edge, said left side panel at a left edge, and said inseam panel at a right edge.

11. The device of claim 7 wherein said crotch panel, said seat panel, said right front panel, said left front panel, said right back panel, and said left back panel have a greater elasticity than said right side panel, said left side panel, and said inseam panel.

12. The device of claim 5, wherein said first stitch type is a flat-lock stitch.

13. A wearable orthopedic device, comprising:
a waistband;
a right leg comprising a right side panel, a right front panel, and a right back panel;
a left leg comprising a left side panel, a left front panel, and a left back panel;
an inseam panel;
a crotch panel; and
a seat panel, and
wherein said crotch panel, said seat panel, said right front panel, said left front panel, said right back panel, and said left back panel comprise a single-layer fabric, wherein said right side panel, said left side panel, and said inseam panel comprise a double-layer fabric including an interior fabric and an exterior fabric, wherein said right side panel extends vertically from a right side of said waistband to a bottom of a right side of said right leg, wherein said left side panel extends vertically from a left side of said waistband to a bottom of a left side of said left leg, and wherein said single-layer fabric has a greater elasticity than said double-layer fabric and is configured to reduce internal rotation of a wearer's femurs, and wherein seams along edges of said right side panel, said left side panel, and said inseam panel to other portions of said device comprise a first stitch type, and seams not along an edge of said right side panel, said left side panel, and said inseam panel comprise a second stitch type, wherein said first stitch type comprises a higher thread density than said second stitch type.

14. The device of claim 13 wherein said crotch panel is located on the anterior of said device and directly connected along a center front portion of said waistband.

15. The device of claim 14 wherein said seat panel is located on a posterior of said device and directly connected along a back portion of said waistband from said right side panel to said left side panel.

16. The device of claim 15 wherein said inseam panel extends along a bottom of said device from a bottom of a left side of said right leg to a bottom of a right side of said left leg, said inseam panel directly connected between said crotch panel and said seat panel.

17. The device of claim 15 wherein said right front panel is on the anterior of said device directly connected along a right front portion of said waistband from said crotch panel to said right side panel and directly connected to a right side of said inseam panel, said right front panel extending to a bottom of a front side of said right leg, and wherein said left front panel is on the anterior of said device directly connected along a left front portion of said waistband from said crotch panel to said left side panel and directly connected to a left side of said inseam panel, said left front panel extending to a bottom of a front side of said left leg.

18. The device of claim 15 wherein said right back panel is on the posterior of said device directly connected to said seat panel at a top edge, said right side panel at a right edge, and said inseam panel at a left edge, and wherein said left back panel is on the posterior of said device directly connected to said seat panel at a top edge, said left side panel at a left edge, and said inseam panel at a right edge.

19. The device of claim 15 wherein said crotch panel, said seat panel, said right front panel, said left front panel, said right back panel, and said left back panel have a greater elasticity than said right side panel, said left side panel, and said inseam panel.

20. The device of claim 13, wherein said first stitch type is a flat-lock stitch.

* * * * *